(12) United States Patent
Mingzhong et al.

(10) Patent No.: US 6,982,097 B2
(45) Date of Patent: Jan. 3, 2006

(54) BIOCIDAL COMPOSITIONS AND METHODS OF USING SAME

(75) Inventors: Su Mingzhong, Kennesaw, GA (US); Long Truong Hoang, Stone Mountain, GA (US); Linh Truong Hoang, Stone Mountain, GA (US)

(73) Assignee: Sani-Care Salon Products, Inc., Lilburn, GA (US)

( * ) Notice: Subject to any disclaimer, the term of this patent is extended or adjusted under 35 U.S.C. 154(b) by 56 days.

(21) Appl. No.: 10/620,281

(22) Filed: Jul. 15, 2003

(65) Prior Publication Data

US 2005/0013878 A1    Jan. 20, 2005

(51) Int. Cl.
*A01N 59/00* (2006.01)
*A01N 59/08* (2006.01)
*A01N 41/02* (2006.01)
*A01N 41/06* (2006.01)
*A01N 43/36* (2006.01)
*A01N 43/50* (2006.01)
*A01N 43/66* (2006.01)
*A01N 25/22* (2006.01)
*C02F 1/50* (2006.01)
*C02F 1/76* (2006.01)

(52) U.S. Cl. ...................... 424/723; 424/661; 424/662; 424/663; 424/664; 424/665; 514/241; 514/389; 514/390; 514/391; 514/398; 514/424; 514/425; 514/553; 514/554; 514/555; 514/556; 514/557; 514/558; 514/559; 514/560; 514/561; 514/568; 514/569; 514/570; 514/571; 514/572; 514/573; 514/574; 514/575; 514/576; 514/577; 514/578; 514/605; 514/970; 210/754; 210/755; 210/756; 504/151

(58) Field of Classification Search ............... 424/723, 424/661, 665, 662–663; 514/241, 398, 424, 514/553–561, 568–578, 970, 389–391, 425, 514/605; 210/754–756; 504/151
See application file for complete search history.

(56) References Cited

U.S. PATENT DOCUMENTS

| | | | |
|---|---|---|---|
| 2,815,311 A | 12/1957 | Ellis et al. | 167/18 |
| 3,975,271 A | 8/1976 | Saunier et al. | 210/62 |
| 4,119,535 A | 10/1978 | White et al. | 210/62 |
| 4,536,389 A | 8/1985 | White et al. | 424/44 |
| 4,698,165 A | 10/1987 | Theyson | 210/755 |
| 4,822,512 A * | 4/1989 | Auchincloss | 424/613 |
| 5,114,647 A | 5/1992 | Levesque et al. | 264/115 |
| 5,464,636 A | 11/1995 | Hight et al. | 424/661 |
| 5,476,670 A | 12/1995 | Hight et al. | 424/661 |
| 5,527,547 A | 6/1996 | Hight et al. | 424/661 |
| 5,603,941 A | 2/1997 | Farina et al. | 424/405 |
| 5,662,940 A | 9/1997 | Hight et al. | 424/661 |
| 5,719,100 A | 2/1998 | Zahradnik et al. | 502/417 |
| 5,753,602 A | 5/1998 | Hung et al. | 510/192 |
| 6,184,192 B1 | 2/2001 | Klinkhammer | 510/191 |
| 6,478,972 B1 * | 11/2002 | Shim et al. | 210/755 |
| 6,524,540 B1 | 2/2003 | Heinig, Jr. | 422/211 |

\* cited by examiner

*Primary Examiner*—John Pak
(74) *Attorney, Agent, or Firm*—Morris Manning & Martin; Tim Tingkang Xia, Esq.

(57) ABSTRACT

This invention relates to biocidal compositions and methods of using same. Also provided is a process for the manufacturing of a biocidal composition in the form of a tablet and a method of using the biocidal compositions for the disinfection of water that may contain microorganisms and biofilms.

28 Claims, No Drawings

BIOCIDAL COMPOSITIONS AND METHODS OF USING SAME

FIELD OF THE INVENTION

This invention relates generally to biocidal compositions and methods of using same for disinfecting and sanitation, more specifically, this invention relates to such biocidal compositions formed in the form of tablets.

BACKGROUND OF THE INVENTION

A disinfectant for water is a substance that destroys or eliminates infectious or other undesirable bacteria, pathogenic fungi, and viruses in water. Disinfectants kill the growing forms but not necessarily the resistant spore forms of microorganisms. Sanitizers are used to reduce the number of living bacteria in water.

A good disinfectant or biocide program is important for proper performance of a whirlpool spa system, pools, toilets, fountains and the like. Common oxidizing biocides such as chlorine, bromine and chlorine dioxide are routinely used. When properly applied, these compounds are useful for controlling the wide range of microorganisms including bacteria, slime, algae, fungi, and protozoa that prevail in such water systems.

Halogen compounds are usually accepted as the most effective disinfecting or biocidal agents for water systems. They are widely used in pool and spa industries. Typically, it is customary to treat biologically contaminated water with one or more biocides to control the population of microorganisms in the water, to prevent fouling of heat exchanger surfaces, and to prevent the spread of disease. The biocides most commonly used to disinfect and sanitize water in water systems are chemicals that generate various halogen species, e.g. hypochlorite or hypobromide, when dissolved in water. There are many hypochlorite-generating chemicals, but the more common ones are chlorine gas, alkali metal hypochlorites such as sodium hypochlorite, alkaline earth metal hypochlorites such as calcium hypochlorite, chlorinated and brominated hydantoins, and chlorinated isocyanuric acid derivatives.

However, the use as such agents are limited due to, among other things, difficulties in storage, mixing, and handling of concentrated halogens. The use of sodium dichloroisocyanurate as a disinfecting agent is also known as shown in U.S. Pat. Nos. 4,536,389 to White et al. and 5,114,647 to Levesque et al. Sodium dichloroisocyanurate hydrolyses in water to produce hypochlorous acid (HOCl) and hypochlorite (OCl), which exist in solution at an equilibrium that is dependent upon the pH of the solution.

Bromide also has been used as a disinfectant. The hypobromous acid and hypobromite species are produced in solution typically by the use of bromo, chloro-5,5-dimethylhydantoin. One reason why bromine sanitizers have gained popularity for indoor pool and spa applications is that the odor of the bromines, formed by reaction of hypobromite species with nitrogenous wastes, is less objectionable to the consumer. Bromine sanitizers, however, have not been popular for outdoor pools because the hypobromite species are rapidly dissipated in sunlight and the sanitizer costs are considerably higher than chlorine sanitizers with cyanuric acid.

Alternatively, potassium monopersulfate and sodium bromide have been marketed together as a bromine sanitizer system for spa applications. The recommended practice is to dose the spa water with sodium bromide (usually as a solution) and then add the recommended dosages of potassium monopersulfate as needed. However, these suffer from the problem that their use can be cost prohibitive.

The water in swimming pools, hot tubs and spas must be sanitized in order to control disease-spreading microorganisms. The toxicity and odor of compounds used to treat the water must be extremely low.

Therefore, a heretofore-unaddressed need exists in the art to address the aforementioned deficiencies and inadequacies.

SUMMARY OF THE INVENTION

Embodiments of the present invention provide biocidal compositions and methods for treating water. Other embodiments provide processes for making the biocidal compositions in the form of tablets.

In one aspect of the present invention, a biocidal composition is provided that includes a filler in an amount of about 50% by weight; an organic acid in an amount of about 20% by weight; sodium bromide in an amount of about 10% by weight; and a halogen-releasing compound in an amount of about 10% by weight. The composition may further include an optional surfactant composition such as a surfactant and a halogen scavenger in an amount of about 4% by weight. In various aspects of the invention, the composition can further include a fragrance and/or a dye. In separate embodiments, the composition of the present invention can be formulated as a powder, a capsule or a tablet.

In various alternative embodiments of another aspect of the present invention, the biocidal composition includes a filler in an amount of about 25% to about 75% by weight; an organic acid in an amount of about 10% to about 40% by weight; sodium bromide in an amount of about 5% to about 15% by weight; and a halogen-releasing compound in an amount of about 1% to about 15% by weight. Additionally, the composition may include an optional surfactant composition in an amount of about 1% to about 10% by weight.

In still other embodiments of the present invention, the biocidal composition can be formulated with a filler, an organic acid, sodium bromide, a halogen-releasing compound and a surfactant.

If the composition is formulated into tablet, the composition can include a tablet-binding agent. In embodiments in which the composition is formulated into a tablet, the binding agent included in the composition can be magnesium stearate, calcium stearate, talc, wax, alkali earth metal carbonates, bicarbonates, or any mixture thereof.

In various embodiments, the filler used in formulating the biocidal composition of the present invention can be sodium bicarbonate, sodium chloride, sodium sulfate, sodium carbonate, sodium tripolyphosphate, borax, zinc sulphate, or any mixture thereof.

In other embodiments, the biocidal composition can include various organic acids such as formic acid, acetic acid, propionic acid, butyric acid) valerie acid, caproic acid, caprylic acid) capric acid, laurie acid, myristic acid, palmitic acid, stearic acid, oleic acid, linoleic acid, linolenic acid, cyclohexanecarboxylic acid, phenylacetic acid, benzoic acid, o-toluic acid, m-toluic acid, p-toluic acid, o-chlorobenzoic acid, m-chlorobenzoic acid, p-chlorobenzoic acid, o-bromobenzoie acid, m-bromobenzoic acid, p-bromobenzoic acid, o-nitrobenzoic acid, m-nitrobeuzoic acid, p-nitrobenzoic acid, pluhalic acid, isophthalic acid, tereplitalic acid, salicylic acid, p-hydroxybenzoic acid, anthranilic acid, m-aminobenzoic acid, p-aminobenzoic acid, o-methoxybeuzoic acid, m-methoxybenzoic acid, p-naethoxybenzoic (anisic) acid, oxalic acid, malonic acid, succinic acid, glutaric acid, adipic acid, maleic acid, fumaric acid, terephthalic acid, acetyl chloride, propionyl chloride, n-butyryl chloride, n-valeryl chloride, stearoyl chloride, benzayl chloride, p-nirobenzoyl chloride, 3,5-dinitrobenzoyl chloride, acetic anhydride, phthalic anhydride, or any mixture thereof.

In any embodiment of the present invention, the biocidal composition is formulated with a halogen-releasing compound which can be sodium dichloroisocyanurate, trichloroisocyanuric acid, calcium hypochlorite, chlorinated hydantoin, N-chlorinated cyanuric acid derivatives, N-chlorosuccinimide, sodium p-toluenesulfochloramine, dichlorosuccinimide, bromochloro-methyl-ethyl-hydantoin, bromochlorodimethyl-hydantoin, 1,3-dichloro-5,5-dimethylhydantoin, alkaline earth metal hypochlorites, or any mixture thereof.

Furthermore, in any embodiment of the present invention, the biocidal composition is formulated with a surfactant which can be alkali metal salts of alkyl substituted benzene sulfonic acids, alkali metal salts of long chain fatty sulphates, alkali metal ether sulfates derived from alcohols and alkyl phenols, alkali metal sulfosuccinates, alkali metal sarcosinates, alkali metal taurides, or any mixture thereof.

Still another aspect of the present invention relates to a process for the preparation of a biocidal water treatment tablet that includes mixing a filler in an amount of about 50% by weight, an organic acid in an amount of about 20% by weight, a disinfectant in an amount of about 10% by weight, a halogen-releasing compound in an amount of about 10% by weight, a surfactant, and a tablet binding agent to form a dry particulate blend. The blend is then fed into an appropriately shaped die and then further compacted to form a die-shaped solid tablet.

Yet another aspect of the present invention relates to a method of disinfecting water or water systems. A biocidally effective amount of any biocidal composition of the present invention is added to the water for a sufficient time as to diminish the microorganism population levels in the water.

These and other aspects of the present invention will become apparent from the following description of the preferred embodiment, although variations and modifications therein may be affected without departing from the spirit and scope of the novel concepts of the disclosure.

DETAILED DESCRIPTION OF THE PREFERRED EMBODIMENTS

Various embodiments of the invention are now described in detail. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the compositions and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

Definitions

As used herein, the term "halogen releasing" agent or compound means any compound that will generate an available halogen ion when dissolved in water. The term "available halogen" means the standard form for expressing the strengths or capacities of halogenating chemicals as well as for the doses in which they are applied and for the hypohalite species (HOCl, OCl$^-$, HOBr, OBr$^-$) that remain in the water.

The term "hypohalite species" means hypochlorous acid, hypochlorite ion, hypobromous acid and hypobromite ion. The term "hypochlorite species" means hypochlorous acid and hypochlorite ion. The term "hypobromite species" means hypobromous acid and hypobromite ion. The terms "free halogen" and "free available halogen" are used interchangeably and are defined as the concentration of halogen existing in the water as hypohalous acid, HOX, and hypohalite ion, OX$^-$, where X is Cl or Br. The terms "free bromine" and "free available bromine" are used interchangeably and are defined as the concentration of bromine existing in the water as hypobromous acid, HOBr, and hypobromite ion, OBr$^-$.

The term "chlorinated isocyanuric acid derivative" means chlorinated isocyanuric acid including dichlorinated and trichlorinated isocyanuric acid, alkali metal and alkaline earth metal salts of chlorinated isocyanuric acid, and hydrates, complexes and mixtures thereof.

The term "hydantoin derivative" means an unsubstituted, halogenated (i.e. chlorinated or brominated), or alkylated hydantoin.

The terms "biocidal", "disinfect" or "disinfecting" include the killing, inhibiting the growth of or inactivation of pathogenic and other microorganisms, such as bacteria, viruses, fungi, and protozoa that pollute water supplies.

A "biocidially effective amount" means the amount of any composition disclosed herein that will disinfect, inactivate or significantly diminish the population of a microorganism.

The "sufficient time as to diminish the microorganism population levels" refers to the time period determined empirically necessary to disinfect or diminish a microorganism level to an acceptable level in a water source.

The terms "inactivate", "inactivation" or "diminishing the population" include rendering a microorganism non-pathogenic pathogenic to humans or other animals, for example, by killing the microorganisms.

The term "microorganism" includes bacteria, fungi, protozoa, viruses and other biological entities and pathogenic species that can pollute water supplies. Examples of microorganisms include, but are not limited to, bacteria such as *Escherichia coli, Streptococcus faecalis, Legimella pneumophila, Yersinia enterocolitica, Staphylococcus aureus, Pseudomonas aeruginosa Klebsiella terrigena* and *Salmonella typhi*. Examples of viruses, include, but are not limited to, hepatitis A and other viruses that are advantageous to inactivate. Examples of fungi include but are not limited to many species, including those that are not pathogenic but are advantageously removed to improve the aesthetic properties of the water. Examples of protozoa include but are not limited to *Enteroamoebae, Giardia,* and *Cryptosporidium parvum*.

Biocidal Compositions

In one aspect of the present invention, a biocidal composition is provided that comprises:
 (a) a filler in an amount of about 50% by weight;
 (b) an organic acid in an amount of about 20% by weight;
 (c) sodium bromide in an amount of about 10% by weight; and
 (d) a halogen-releasing compound in an amount of about 10% by weight.

Additionally, the composition may further have an optional surfactant in an amount of about 4% by weight.

In an alternative embodiments of the present invention, the biocidal composition comprises:
 (a) a filler in an amount of about 25% to about 75% by weight;
 (b) an organic acid in an amount of about 10% to about 40% by weight;
 (c) sodium bromide in an amount of about 5% to about 15% by weight; and
 (d) a halogen-releasing compound in an amount of about 5% to about 15% by weight.

Additionally, the composition may further have an optional surfactant composition in an amount of about 1% to about 10% by weight.

In yet another embodiment, the biocidal composition comprises:
 (a) a filler;
 (b) an organic acid;
 (c) sodium bromide;
 (d) a halogen-releasing compound; and
 (e) an optional surfactant.

Fillers

One component of the biocidal composition of the present invention is a particulate filler such as alumina, talc, silica and the like. Alumina, in particular, is used is specific embodiments when a release control agent is desired. Alumina has a slow dissolution characteristics to give the composition a sustained release functionality. Generally the filler will comprise from about 25% by weight to about 75% by weight of the total weight of the composition. Preferably, the filler will comprise about 50% by weight of the composition.

Specific examples of suitable fillers include, but are not limited to, alumina, sodium bicarbonate, sodium chloride, potassium chloride, calcium chloride, calcium sulfate, sodium sulfate, potassium sulfate, sodium citrate, sodium acetate, sodium carbonate, potassium fluoride, sodium tripolyphosphate, borax, zinc sulphate, and mixtures thereof.

Organic Acids

The biocidal compositions of the present invention also include an organic acid. In various embodiments, the organic acid is present in an amount of about 10% to about 40% total weight of the composition. Preferably, the organic acid is present in an amount about 20% by total weight of the composition. One skilled in the art will recognize that there are many organic acids that can be incorporated into the compositions of the present invention. Examples of sach organic acids include, but are not limited to, formic acid, acetic acid, propionic acid, butyric acid, valeric acid, caproic acid, caprylic acid, capric acid, lauric acid, myristic acid, palmitic acid, stearic acid, oleic acid, linoleic acid, linolenic acid, cyclohexanecarboxylic acid, phenylacetic acid, benzoic acid, o-roluic acid, m-taluic acid, p-toluic acid, o-chlorobenzoic acid, m-chlorobenzoic acid, p-chlorobenzoic acid, o-bromobenzoic acid, m-bromobenzoic acid, p-bronaobenzoic acid, o-nitrobenzoic acid, mn-nitrobenzoic acid, p-nitrobenzoic acid, phthalic acid, isophihalic acid, terephtalic acid, salicylic acid, p-hydroxybenzoic acid, anthranilic acid, m-aminobenzoic acid, p-aniinobenzoic acid, o-methoxybenzoic acid, m-methoxytenzoic acid, p-medioxybenzoic (anisic) acid, oxalic acid, malonic acid, succinic acid, glutaric acid, adipic acid, maleic acid, fumaric acid, terephthalic acid, acetyl chloride, propionyl chloride, n-biztyryl chloride, n-valeryl chloride, stearoyl chloride, beozoyl chloride, p-nitrobeazoyl chloride, 3,5-dinitrobenzoyl chloride, acetic anhydride, and phthalic anhydride. One skilled in the art will also recognize tat various mixtures of organic acids can be used as well without parting from the scope of the present invention.

Halogen-Releasing Agents

Hypobromous acid (HOBr) and the hypobromite species are typically generated from either bromine and N-bromo organic compounds or by reacting a bromide salt with a solution of hypochlorous acid or other oxidizing agents. These are typically more effective biocides than hypochlorous acid. As a non-limiting example, under some conditions, this superiority is quite dramatic. In particular, hypobromous acid is known to react with ammonia to produce bromamines. Bromamines, unlike chloramines, have very good biocidal activity and have a more acceptable odor. In addition, hypobromite species are more effective than hypochlorite species at pH values above 7.5 due to the higher pK value for the equilibrium shift from hypobromous acid to hypobromite ion.

In most cases where hypobromous acid is used as a biocidal agent, the hypobromous acid generating composition contains a large weight percentage of bromine. Liquid bromine, for example, is 100% bromine by weight and 1-bromo-3-chloro-5,5-dimethylhydantoin is 32.8% bromine by weight. Even though hypobromous acid is generally superior to hypochlorous acid, the higher cost of bromine has limited the use of bromine-based biocides.

Currently available dry sources of hypobromous acid suffer from a number of disadvantages in addition to their higher cost. The hydantoin products such as 1-bromo-3-chloro-5,5-dimethylhydantoin, 1,3-dichloro-5,5-dimethylhydantoin, 1,3-dibromo-5,5-dimethylhydantoin, 1,3-dichloro-5-ethyl-5-methylhydantoin, and 1-bromo-3-chloro-5-ethyl-5-methylhydantoin typically have very low dissolution rates.

In addition, the hydantoin products are not as effective biocides as might be expected based on the amount of hypobromous acid formed, because these products also release large amounts of 5,5-dimethylhydantoin or 5-ethyl-5-methylhydantoin into the water, eventually leading to their buildup of high concentrations in the water. High concentrations of these products inhibit the biocidal activity of the hypobromous acid as has been previously noted in U.S. Pat. No. 4,698,165.

As an alternative to the hydantoins, hypobromous acid may be prepared by reacting a bromide salt with a source of hypochlorite species according to the following equation:

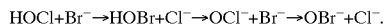
$HOCl+Br^- \rightarrow HOBr+Cl^- \rightarrow OCl^- +Br^- \rightarrow OBr^- +Cl^-$.

See for example, U.S. Pat. Nos. 2,815,311, 3,975,271, and 4,119,535, which are herein incorporated by reference. The hypobromous acid formed is the active biocide. However, in the process of killing microorganisms or oxidizing organic material, the hypobromous acid is reduced to form bromide ion.

Thus, the bromide ion can be reused to generate more hypobromous acid by reaction with hypochlorite species. Because the bromide ion is continuously reused, only small amounts of bromide ion are necessary to make a halogen-based biocide in combination with bromide salts in order to perform as a biocide of the present invention.

The amount of bromide salt incorporated into the biocidal composition of the present invention is added in the amount of about 5% to about 15% total weight. Preferably, the bromide salt. is present in an amount of about 10% total weight of the composition.

The amount of the halogen-releasing agent incorporated into the biocidal composition of the present invention is added in the amount of about 5% to about 15% total weight. Preferably, the halogen-releasing agent is present in an amount of about 10% total weight of the composition.

Thus, the halogen donor or releasing agent of the present invention can include, but is not limited to, sodium dichloroisocyanurate, trichloroisocyanuric acid, calcium hypochlorite, chlorinated hydantoin, N-chlorinated cyanuric acid derivatives, N-chlorosuccinimide, sodium p-toluenesulfochloramine, dichlorosuccinimide, bromochloro-methyl-ethyl-hydantoin, bromochlorodimethyl-hydantoin, 1,3-dichloro-5,5-dimethylhydantoin, alkaline earth metal hypochlorites, and mixtures thereof.

Surfactants

The biocidal composition of the present invention also optionally incorporates the use of a surfactant or a surfactant composition. The surfactant can serves as a release control material or can be used to create denser, more compacted tablets at decreased tablet pressures. Suitable surfactants useful in the process of the present invention are selected from the group consisting of the alkali metal salts of alkyl substituted benzene sulphonic acids, alkali metal salts of long chain fatty sulphates, alkali metal ether sulphates derived from alcohols and alkyl phenols, alkali metal sulfosuccinates, alkali metal sarcosinates and alkali metal taurides and mixtures thereof.

One skilled in the art will readily understand that a surfactant need only be incorporated in small amounts to sufficiently provide the appropriate compaction. Preferably, the surfactant will comprise from about 1.0% to about 10% by total weight, and most preferably about 4.0% by weight of the total weight of the composition. A halogen scavenger can also be used in the surfactant composition, preferably at molar ratio with surfactant of 1:3. In one embodiment, a halogen scavenger is selected from a hydantoin group.

Process for the Manufacture of a Biocidal Tablet

The biocidal compositions of the present invention are preferably formulated into a form which can be easily handled, and which may be used advantageously to practice the present inventive methods. Exemplary of such forms would include the following: a tablet, a capsule, a powder, a suspension or a dispersion. Preferably, the compositions of the present invention are manufactured into a tablet-like form. Tablets are thought preferable due to their ease of manufacture, and their ease of use. In this regard, tablets could easily be prepared and placed in a format such as a blister pack container, if so desired, which includes instructions for practicing the water sanitizing methods of the present invention.

Thus, another embodiment of the present invention provides a process for making a biocidal water treatment tablet comprising the steps of:

(a) mixing a filler in an amount of about 50% by weight, an organic acid in an amount of about 20% by weight, a disinfectant in an amount of about 10% by weight; a halogen-releasing compound in an amount of about 10% by weight; an optional surfactant composition, and a tablet binding agent to form a dry particulate blend;

(b) feeding said blend into an appropriately shaped die; and (c) compacting said blend at a conventional tabletting pressure to form a die-shaped solid tablet.

The process of the present invention comprises the compression of the free flowing dry particulate ingredients hereinbefore mentioned into tablet as is known in the art. The ingredients are first mixed together in their appropriate ratios to make a uniform blend. The mixture is fed into an appropriately shaped die and a compression member is then forced into the die to form a shaped body. Conceivably, the tablets could also be formed by means of an extrusion process whereby the mixture of ingredients are fed into an extruder which compresses them into a continuous rod of solid composition which is then cut into the appropriately sized pieces.

The addition of the surfactant as described herein, allows for the production of a more tightly compressed tablet under the same pressure. This could enhances the sustained controlled dissolution rate as well as curtailing the wear and tear of the tabletting machines since less pressure is required to yield a sufficiently compressed tablet.

The pressure under which the biocidal tablet powder is compressed is important since, if the pressure is too low, the tablet components are not tightly bound to a sufficient degree and will tend to dissolve and release the active agents too rapidly resulting in a shortened use life. Alternatively, if the compactor pressure is too high, the tablet tends to dissolve and release the active too slowly ultimately resulting in insufficient cleaning action. As one skilled in the art will recognize, the actual pressure that is appropriately employed depends on the components used, their relative proportions and the dissolution rate of the tablet desired.

The biocidal compositions of the present invention in the tablet form have been successfully made and used. In one exemplary test, a tablet with a weight of about 10 to 20 grams according to the present invention was put into a foot spa with about 1 to 3 gallons of water. The foot spa was cleaned and sanitized substantially equivalent to being cleaned by 6 to 8 gallons of water.

The biocidal composition of the present invention can incorporate a tablet-binding agent in order to aid in the compaction process and insure that the solid biocidal tablet is readily released from the die with its integrity maintained. Suitable tablet-binding agents include, but are not limited to, magnesium stearate, calcium stearate, talc, alkali earth metal carbonates, bicarbonates, and mixtures thereof.

Other optional ingredients may be added to the biocidal composition of the present invention include, but are not limited to, dyes, fragrances, anti-caking agents, stabilizers, and the like.

Method for Using the Biocidal Compositions for the Treatment of Water

Another embodiment of the current invention is a method of disinfecting water comprising the step of adding to the water a biocidal effective amount of a biocidal composition for a sufficient time as to diminish the microorganism population levels in the water. The biocidal composition can be any biocidal composition disclosed herein. One skilled in the art will easily recognize that the time necessary to expose the water to the compositions of the present invention can be determined empirically based upon such factors as, but not limited to, the amount and species of microorganism(s) present, the volume of water to be treated, the source of the water to be treated, and the water temperature.

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention.

We claim:

1. A biocidal composition comprising:
   (a) a filler in an amount of about 50% by weight;
   (b) an organic acid in an amount of about 20% by weight;
   (c) sodium bromide in an amount of about 10% by weight; and
   (d) a halogen-releasing compound in an amount of about 10% by weight.

2. The composition of claim 1 further comprising a fragrance.

3. The composition of claim 1 further comprising a dye.

4. The composition of claim 1, wherein the composition is a powder.

5. The composition of claim 1, wherein the composition is a capsule.

6. The composition of claim 1, wherein the composition is a tablet.

7. The composition of claim 6 further comprising a tablet-binding agent.

8. The composition of claim 6, wherein the tablet-binding agent is selected from the group consisting of magnesium stearate, calcium stearate, talc, alkali earth metal carbonates, bicarbonates, wax, and mixtures thereof.

9. The composition of claim 1, wherein the filler is selected from the group consisting of alumina, sodium bicarbonate, sodium chloride, potassium chloride, calcium chloride, calcium sulfate, sodium sulfate, potassium sulfate, sodium citrate, sodium acetate, sodium carbonate, potassium fluoride, sodium tripolyphosphate, borax, zinc sulfate, and mixtures thereof.

10. The composition of claim 1, wherein the organic acid is selected from the group consisting of formic acid, acetic acid, propionic acid, butyric acid, valerie acid, caproic acid, caprylic acid, capric acid, laurie acid, myristic acid, palmitic acid, stearic acid, oleic acid, linoleic acid, linolenic acid, cyclohexanecarboxylic acid, phenylacetic acid, benzoic acid, o-toluic acid, m-toluic acid, p-toluic acid, o-chlorobenzoic acid, m-chlorohenzoic acid, p-chlorobenzoic acid, o-bromobenzoic acid, m-bromobenzoic acid, p-bromobenzoic acid, o-nitrobenzoic acid, m-nitrobenzoic acid, p-nitrobenzoic acid, phthalic acid, isoplithalic acid, terephtalic acid, salicylic acid, p-hydroxybenzoic acid, anthranilic acid, m-aminobenzoic acid, p-aminobenzoic acid, o-methoxybenzoic acid, m-methoxybenzoic acid, p-methoxybenzoic (anisic) acid, oxalic acid, malonic acid, succinic acid, glutaric acid, adipic acid, maleic acid, fumaric acid, acetyl chloride, propionyl chloride, n-butyryl chloride, n-valeryl chloride, stearoyl chloride, benzoyl chloride, p-nitrobenzoyl chloride, 3,5-dinitrobenzoyl chloride, acetic anhydride, phthalic anhydride, and mixtures thereof.

11. The composition of claim 1, wherein the halogen-releasing compound is selected from the group consisting of sodium dichloroisocyanurate, trichloroisocyanuric acid, calcium hypochlorite, chlorinated hydantoin, N-chlorinated cyanuric acid derivatives, N-chlorosuccunmide, sodium p-toluenesulfochloramine, dichlorosuccinimide, bromo-chloro-methyl-ethyl-hydantoin, bromochlorodimethyl-hydantoin, 1,3-dichloro-5,5-dimethylhydantion, alkaline earth metal hypochlorites, and mixtures thereof.

12. The composition of claim 1 further comprising an optional surfactant in an amount of about 4% by weight.

13. The composition of claim 12, wherein the surfactant is selected from the group consisting of alkali metal salts of alkyl substituted benzene sulfonic acids, alkali metal salts of long chain fatty sulphates, alkali metal ether sulfates derived from alcohols and alkyl phenols, alkali metal sulfosuccinates, alkali metal sarcosinates, alkali metal taurides and mixtures thereof.

14. The composition of claim 13 further comprising a hydantoin halogen scavenger.

15. A biocidal composition comprising:
   (a) a filler in an amount of about 25% to about 75% by weight;
   (b) an organic acid in an amount of about 10% to about 40% by weight;
   (c) sodium bromide in an amount of about 5% to about 15% by weight; and
   (d) a halogen-releasing compound in an amount of about 5% to about 15% by weight.

16. A method of disinfecting water comprising adding to the water a biocidal effective amount of a biocidal composition for a sufficient time as to diminish the microorganism population levels in the water, wherein the biocidal composition comprises:
   (a) a filler in an amount of about 50% by weight;
   (b) an organic acid in an amount of about 20% by weight;
   (c) sodium bromide in an amount of about 10% by weight;
   (d) a halogen-releasing compound in an amount of about 10% by weight; and
   (e) an optional surfactant composition in an amount up to about 4% by weight.

17. The method of claim 16, wherein the composition further comprises a fragrance.

18. The method of claim 16, wherein the composition further comprises a dye.

19. The method of claim 16, wherein the composition is a powder.

20. The method of claim 16, wherein the composition is a capsule.

21. The method of claim 16, wherein the composition is a tablet.

22. The method of claim 21, wherein the composition further comprises a tablet-binding agent.

23. The method of claim 22, wherein the tablet-binding agent is selected from the group consisting of magnesium stearate, calcium stearate, talc, alkali earth metal carbonates, bicarbonates, and mixtures thereof.

24. The method of claim 16, wherein the filler is selected from the group consisting of alumina, sodium bicarbonate, sodium chloride, potassium chloride, calcium chloride, calcium sulfate, sodium sulfate, potassium sulfate, sodium citrate, sodium acetate, sodium carbonate, potassium fluoride, sodium tripolyphosphate, borax, zinc sulfate, and mixtures thereof.

25. The method of claim 16, wherein the organic acid is selected from the group consisting of formic acid, acetic acid, propionic acid, butyric acid, valeric acid, caproic acid, caprylic acid, capric acid, lauric acid, myristic acid, palmitic acid, stearic acid, oleic acid, linoleic acid, linolenic acid, cyclohexanecarboxylic acid, phenylacetic acid, benzoic acid, o-toluic acid, m-toluic acid, p-toluic acid, o-chlorobenzoic acid, m-chilorobenzoie acid, p-chlorobenzoic acid, o-bromobenzoic acid, m-bromobenzoic acid, p-bromobenzoic acid, o-nitrobenzoic acid, m-nitrobenzoic acid, p-nitrobenzoic acid, phthalic acid, isophthalic acid, terephtalic acid, salicylic acid, p-hydroxybenzoic acid, anthranilic acid, m-aminobenzoic acid, p-aminobenzoic acid, o-methoxybenzoic acid, n-methoxybenzoic acid, p-methoxybenzoic (anisic) acid, oxalic acid, malonic acid, succinic acid, glutaric acid, adipic acid, maleic acid, fumaric acid, acetyl chloride, propionyl chloride, n-butyryl chloride, n-valeryl chloride, stearoyl chloride, benzoyl chloride, p-nitrobenzoyl chloride, 3,5-dinitrobenzoyl chloride, acetic anhydride, phthalic anhydride, and mixtures thereof.

26. The method of claim 16, wherein the halogen-releasing compound is selected from the group consisting of sodium dichloroisocyanurate, trichloroisocyanuric acid, calcium hypochlorite, chlorinated hydantoin, N-chlorinated cyanuric acid derivatives, N-chlorosuccinimide, sodium p-toluenesulfochloramine, dichlorosuccinimide, bromochloro-methyl-ethyl-hydantoin, bromochlorodimethyl-hydantoin, 1,3-dichloro-5,5-dimethylhydantoin, alkaline earth metal hypochlorites, and mixtures thereof.

27. The method of claim 16, wherein the surfactant composition has a surfactant that is selected from the group consisting of alkali metal salts of alkyl substituted benzene sulfonic acids, alkali metal salts of long chain fatty sulfates, alkali metal ether sulfates derived from alcohols and alkyl phenols, alkali metal sulfosuccinates, alkali metal sarcosinates, alkali metal taurides anti mixtures thereof.

28. The method of claim 27, wherein the surfactant composition further comprises a hydantoin halogen scavenger.

\* \* \* \* \*